US008256080B2

United States Patent
Cunningham et al.

(10) Patent No.: US 8,256,080 B2
(45) Date of Patent: Sep. 4, 2012

(54) SYSTEM AND METHOD FOR MANUFACTURING A MEDICAL INSTRUMENT

(75) Inventors: James S. Cunningham, Boulder, CO (US); Douglas A. Higley, Denver, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 863 days.

(21) Appl. No.: 12/359,865

(22) Filed: Jan. 26, 2009

(65) Prior Publication Data
US 2009/0188094 A1 Jul. 30, 2009

Related U.S. Application Data
(60) Provisional application No. 61/024,052, filed on Jan. 28, 2008.

(51) Int. Cl.
*B23P 19/04* (2006.01)
*B25B 27/00* (2006.01)
*B25B 27/14* (2006.01)
*A61B 18/18* (2006.01)
*A61B 1/32* (2006.01)
*A61B 10/00* (2006.01)

(52) U.S. Cl. ............ 29/244; 29/238; 29/239; 29/270; 29/278; 606/51; 606/52; 600/205; 600/206; 600/562; 600/567; 600/568

(58) Field of Classification Search .............. 29/244, 29/238, 239, 270, 278; 606/51, 52; 600/205, 600/206, 562, 567, 568
See application file for complete search history.

(56) References Cited

U.S. PATENT DOCUMENTS

| | | | |
|---|---|---|---|
| 4,662,372 A | 5/1987 | Sharkany et al. | |
| 7,150,097 B2 | 12/2006 | Sremcich et al. | |
| 7,195,631 B2 | 3/2007 | Dumbauld | |
| 7,384,420 B2 | 6/2008 | Dycus et al. | |
| 2003/0229344 A1 | 12/2003 | Dycus et al. | |
| 2004/0243125 A1 | 12/2004 | Dycus et al. | |
| 2004/0249374 A1 | 12/2004 | Tetzlaff et al. | |
| 2006/0167441 A1* | 7/2006 | Wang et al. | 606/1 |
| 2007/0062017 A1* | 3/2007 | Dycus et al. | 29/407.04 |

* cited by examiner

Primary Examiner — Monica Carter
Assistant Examiner — Nirvana Deonauth

(57) ABSTRACT

A system for manufacturing a forceps is disclosed. The system includes a forceps having first and second opposing jaw members. A compression mechanism is coupled to the pair of opposing jaw members and configured to provide and maintain a compression force between the opposing jaw members. The system also includes a load cell configured to measure an initial compression force between the opposing jaw members and a controller coupled to the load cell and configured to adjust the compression force based on a comparison between the initial compression force and a predetermined range.

13 Claims, 6 Drawing Sheets

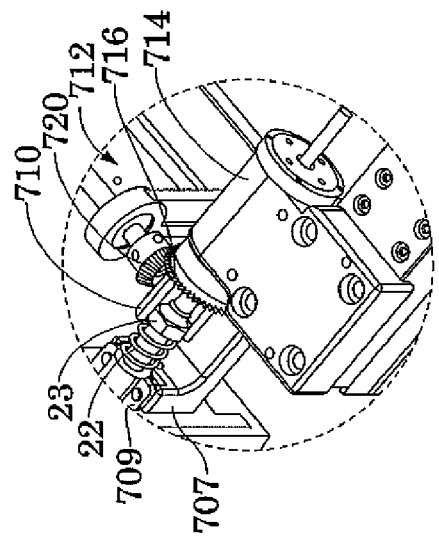
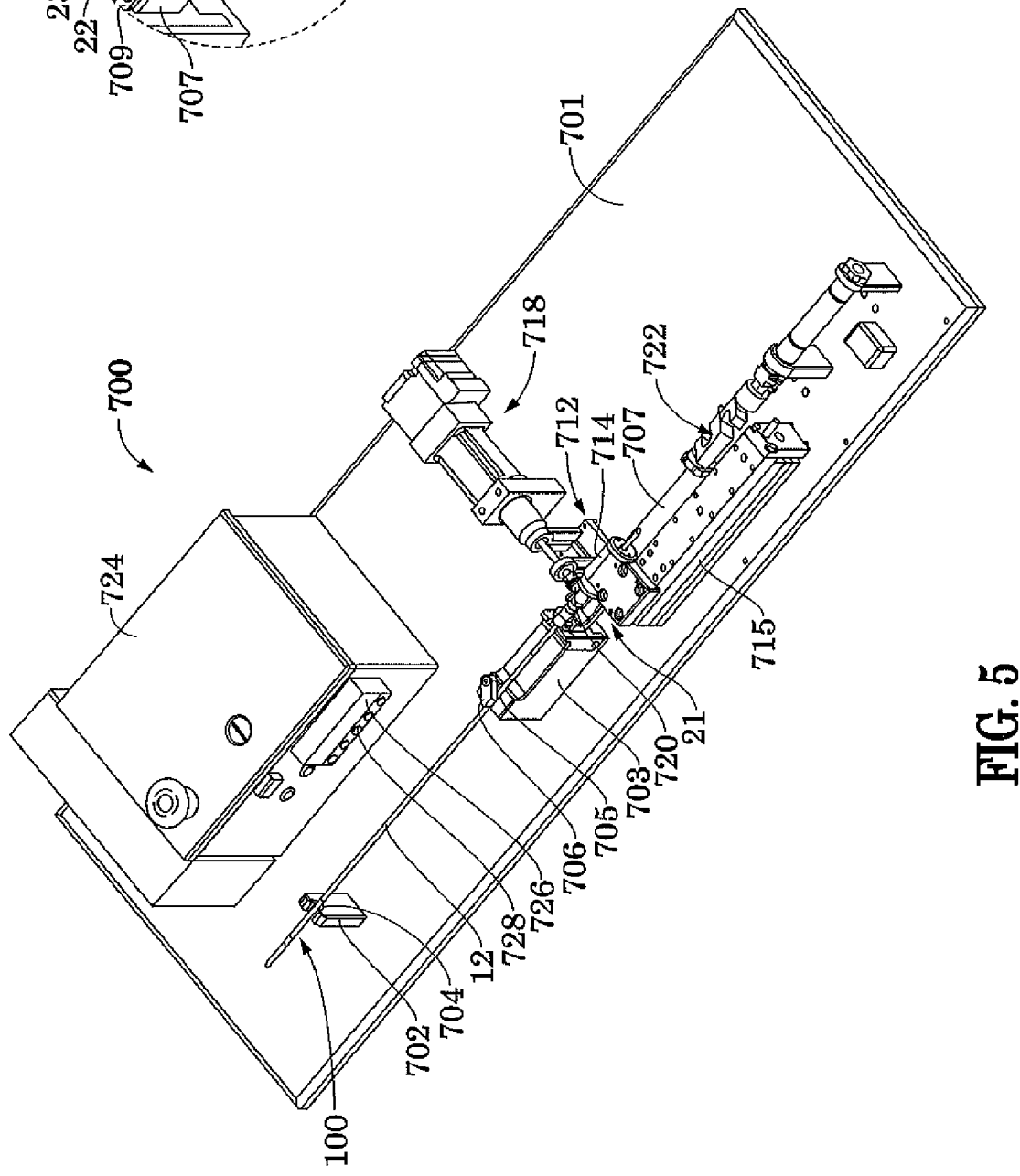
FIG. 6
FIG. 5

SYSTEM AND METHOD FOR MANUFACTURING A MEDICAL INSTRUMENT

CROSS-REFERENCE TO RELATED APPLICATIONS

This application claims the benefit of priority to U.S. Provisional Application Ser. No. 61/024,052 entitled "SYSTEM AND METHOD FOR MANUFACTURING A MEDICAL INSTRUMENT" filed Jan. 28, 2008 by James S. Cunningham et al, which is incorporated by reference herein.

BACKGROUND

1. Technical Field

The present disclosure relates generally to electrosurgical instruments and, more particularly, to an open or endoscopic bipolar electrosurgical forceps and system and method of manufacturing thereof.

2. Background of Related Art

A hemostat or forceps is a simple pliers-like tool that uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complementing traditional open methods of gaining access to vital organs and body cavities with endoscopes and endoscopic instruments which access organs through small puncture-like incisions. Endoscopic instruments are inserted into the patient through a cannula, or port that has been made with a trocar.

By utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

Electrosurgical methods may be able to seal large vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried. Vessel sealing is defined as the process of liquefying the collagen in the tissue so that it reforms into a fused mass. Thus, coagulation of small vessels is sufficient to permanently close them. Larger vessels need to be sealed to assure permanent closure.

In order to properly and effectively seal larger vessels, a greater closure force between opposing jaw members is required. It has been found that the pressure range for assuring a consistent and effective seal is between about 3 kg/cm$^2$ to about 16 kg/cm$^2$ and within a working range of about 7 kg/cm$^2$ to about 13 kg/cm$^2$. Manufacturing an instrument which is capable of providing a closure pressure within this working range has been shown to be effective for sealing arteries and other vascular bundles.

Various force-actuating assemblies have been developed in the past for providing the appropriate closure forces to effect vessel sealing. Due to exact forces that need to be applied to the opposing jaw members, during assembly of the sealing instrument, it would be an advantage to test the closure pressure between sealing surfaces to assure that the closure pressure falls within the preferred pressure range for sealing tissue and vascular bundles. Unfortunately, it has been found that measuring the closure pressure between the sealing surfaces is particularly difficult. For example, one of the inherent difficulties of accurately measuring the closure force includes measuring the closure force in a non-destructive fashion, e.g., placing a measuring device, such as a strain gauge or pressure sensitive film, between the jaw members interferes with the final angle of the jaw members, interfering with the measurement. The measurement device would need to be shaped exactly like the jaw profile in order to measure the pressure accurately. The jaw would have to be free of stop members or only the peaks in pressure would be measured. Moreover, it has been found that manufacturing tolerances of the internal working components of the handle assembly and actuating assemblies may affect the overall closure pressure between the sealing surfaces.

SUMMARY

According to one aspect of the present disclosure, a system for manufacturing a forceps is disclosed. The system includes a forceps having first and second opposing jaw members. The system further includes a compression mechanism coupled to the pair of opposing jaw members and configured to provide and maintain a compression force between the opposing jaw members. The system also includes a load cell configured to measure an initial compression force between the opposing jaw members and a controller coupled to the load cell and configured to adjust the compression force based on a comparison between the initial compression force and a predetermined range.

The present disclosure also provides for a method for manufacturing a forceps. The method includes the step of providing a forceps having first and second opposing jaw members and a compression mechanism coupled to the pair of opposing jaw members. The compression mechanism is configured to provide and maintain a compression force between the opposing jaw members. The method also includes the steps of measuring an initial compression force between the opposing jaw members and adjust the compression force based on a comparison between the initial compression force and a predetermined range.

BRIEF DESCRIPTION OF THE DRAWINGS

Various embodiments of the subject instrument are described herein with reference to the drawings wherein:

FIG. 5 is a perspective view of a system for setting a force of a compression mechanism according to an embodiment of the present disclosure;

FIG. 6 is an enlarged perspective view of the system of FIG. 5; and

DETAILED DESCRIPTION

Figure 1:
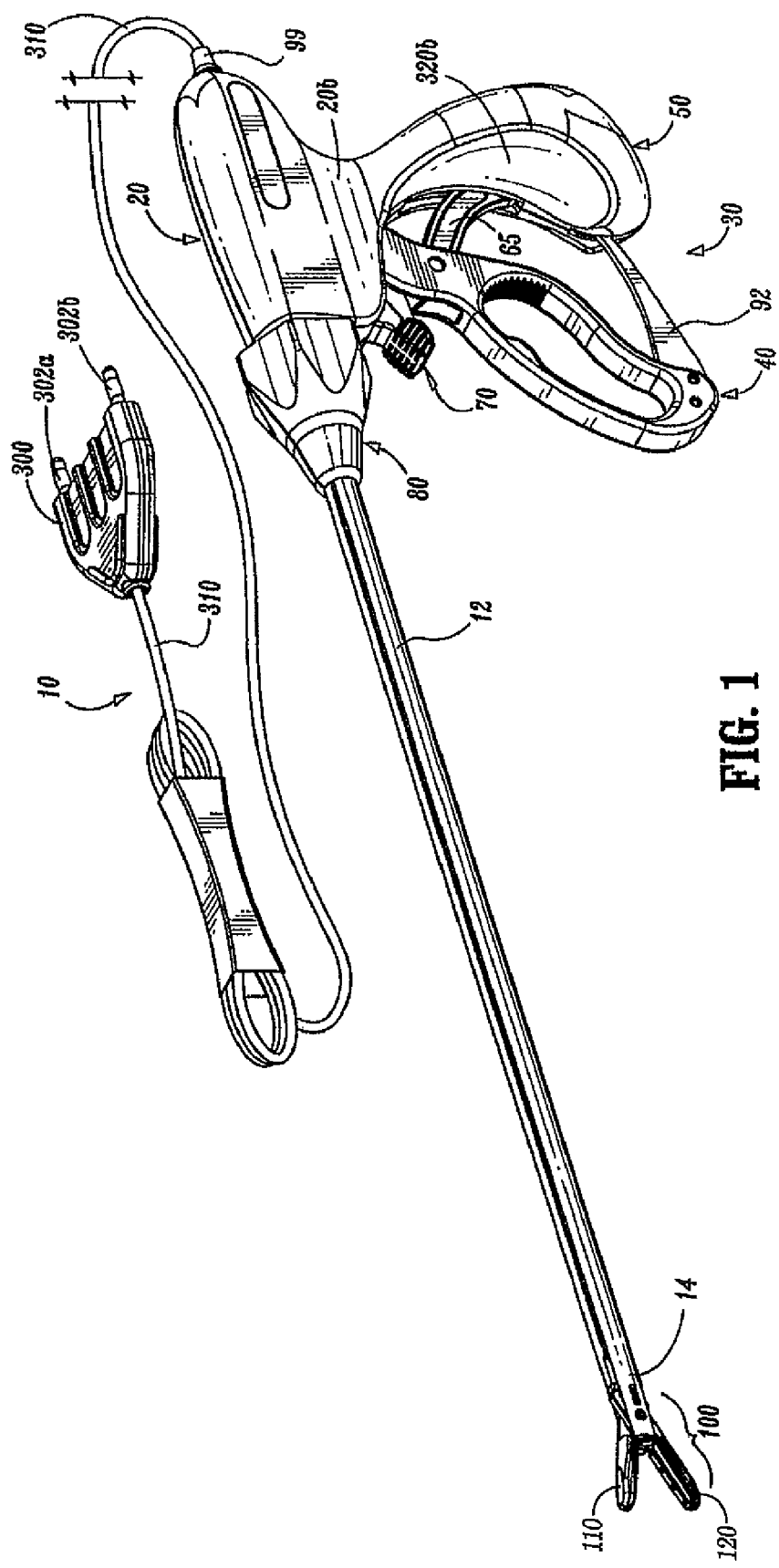
FIG. 1 is a left, perspective view of an endoscopic bipolar forceps showing a housing, a shaft and an end effector assembly according to the present disclosure.

Referring now to FIG. 1, one embodiment of a bipolar forceps 10 is shown for use with various surgical procedures and generally includes a housing 20, a handle assembly 30, a rotating assembly 80, a trigger assembly 70 and an end effector assembly 100 that mutually cooperate to grasp, seal and divide tubular vessels and vascular tissue.

More particularly, forceps 10 includes a shaft 12 that has a distal end 14 dimensioned to mechanically engage the end effector assembly 100 and a proximal end 16 that mechanically engages the housing 20. In the drawings and in the descriptions that follow, the term "proximal", as is traditional, will refer to the end of the forceps 10 that is closer to the user, while the term "distal" will refer to the end that is further from the user.

Figure 3:
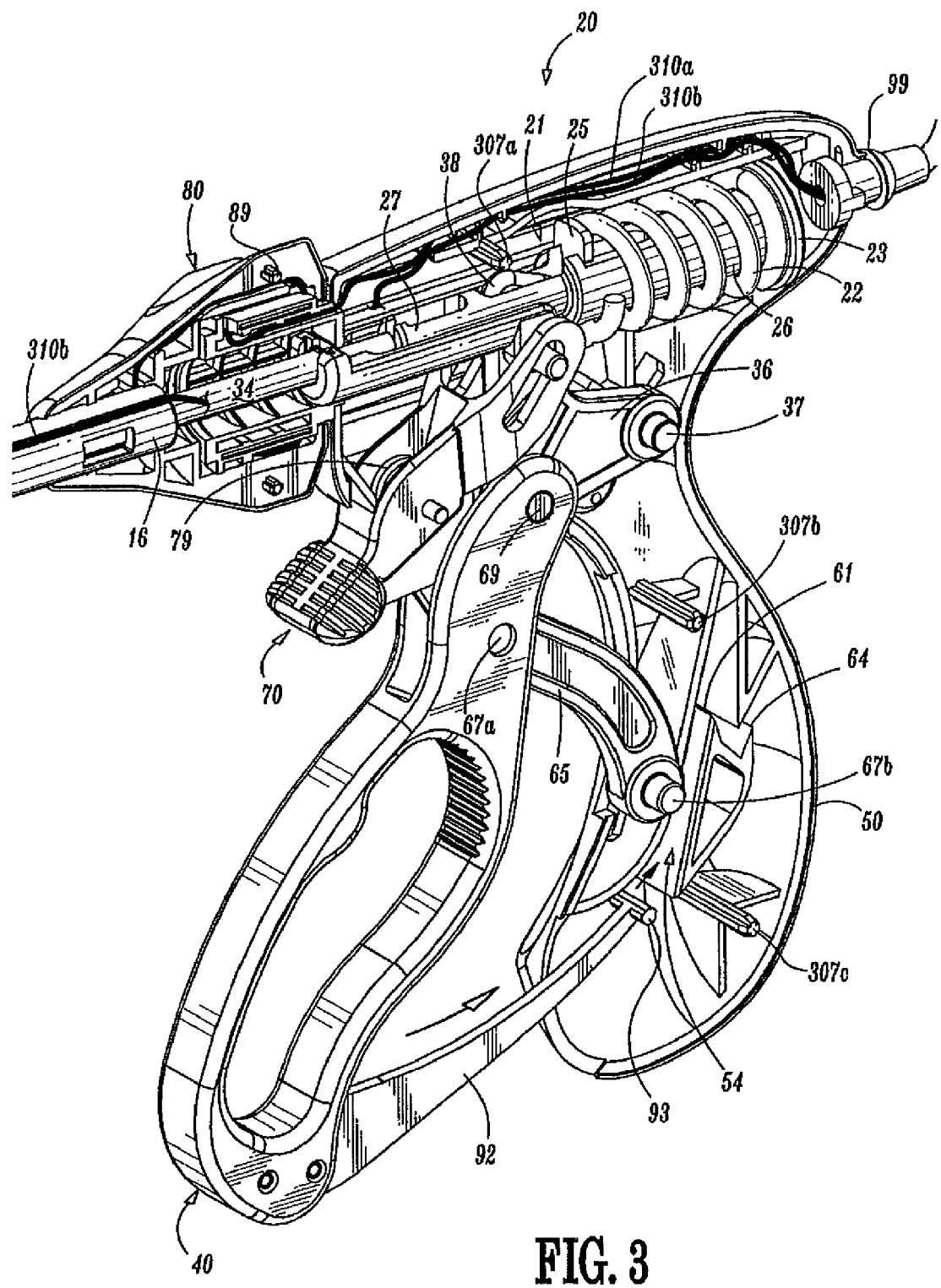
FIG. 3 is an enlarged, left perspective view showing the housing without a cover plate and the internal working components of the forceps disposed therein.

Forceps 10 also includes an electrical interface or plug 300 that connects the forceps 10 to a source of electrosurgical energy, e.g., a generator (not shown). Plug 300 includes a pair of prong members 302a and 302b that are dimensioned to mechanically and electrically connect the forceps 10 to the source of electrosurgical energy. An electrical cable 310 extends from the plug 300 to a sleeve 99 and securely connects the cable 310 to the forceps 10. As best seen in FIG. 3, cable 310 is internally divided into cable lead 310a and 310b that each transmit electrosurgical energy through their respective feed paths through the forceps 10 to the end effector assembly 100 as explained in more detail below.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is attached to a distal end 303 (FIG. 4) of housing 20.

Figure 2:
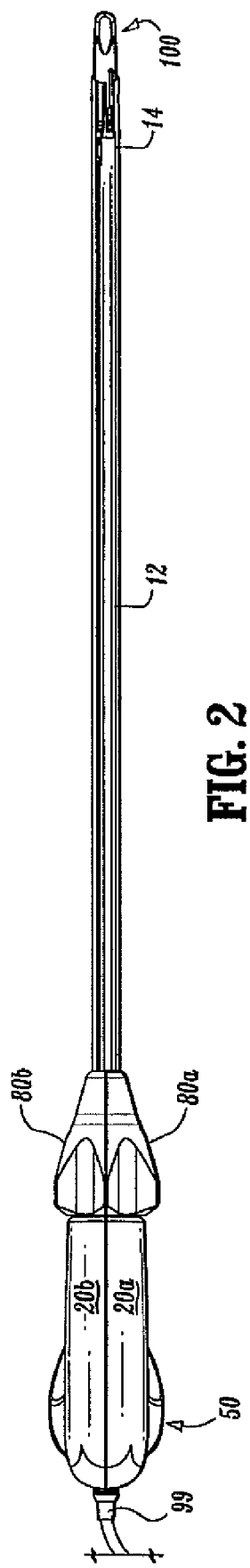
FIG. 2 is a top view of the forceps of FIG. 1.
Figure 4:
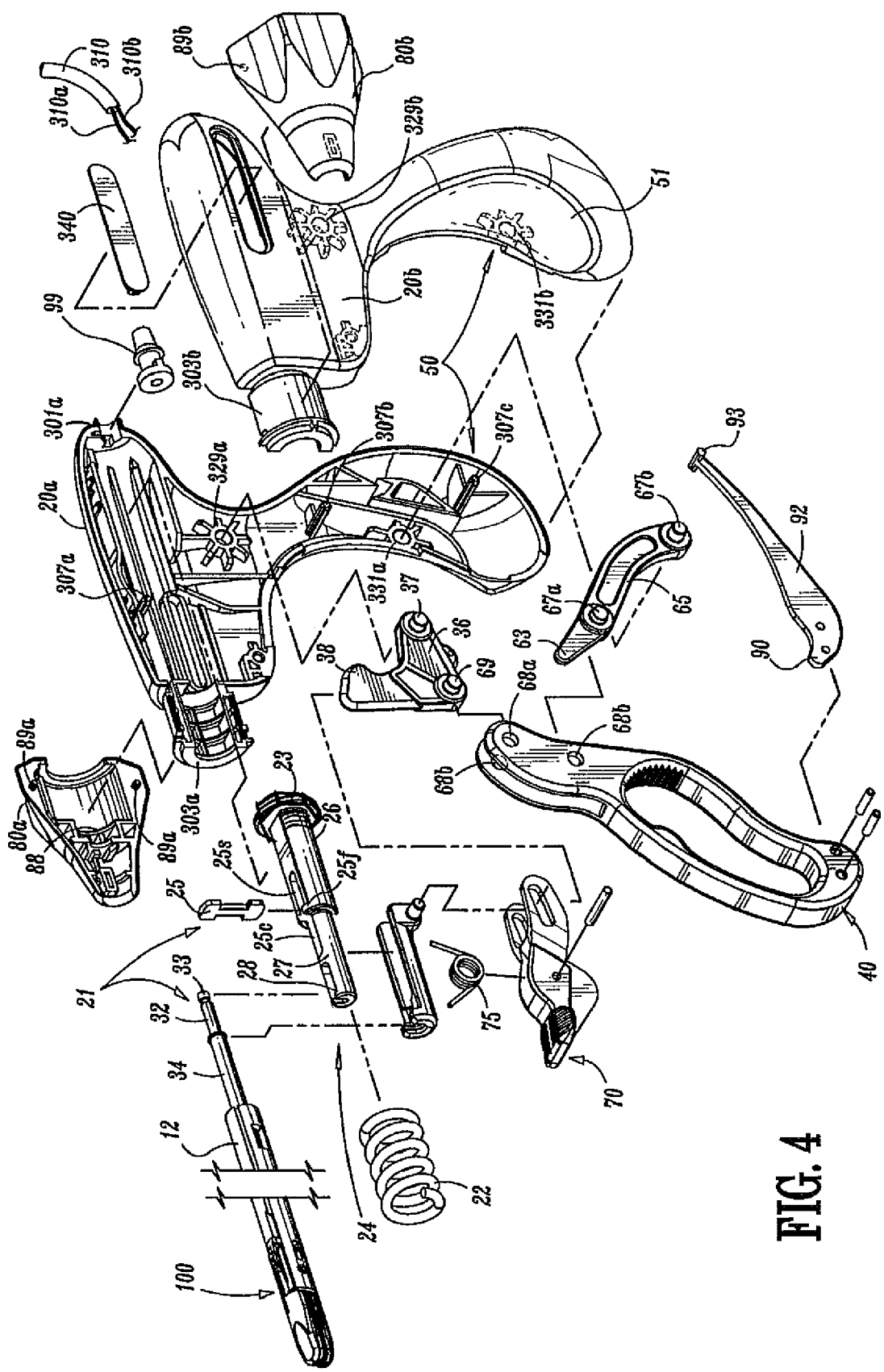
FIG. 4 is an exploded, perspective view of the housing and the internal working components thereof with the attachment of the shaft and end effector assembly to the housing shown in broken line illustration.

As best seen in FIGS. 2 and 4, housing 20 is formed from two (2) housing halves 20a and 20b that each include a plurality of interfaces 307a, 307b and 307c (FIG. 4) that are dimensioned to mechanically align and engage one another to form housing 20 and enclose the internal working components of forceps 10.

Likewise, rotating assembly 80 includes two halves 80a and 80b that, when assembled, enclose and engage the proximal end 16 of shaft 12 to permit selective rotation of the end effector assembly 100 as needed. Half 80a includes a pair of detents 89a (FIG. 4) that are dimensioned to engage a pair of corresponding sockets 89b (shown in phantom in FIG. 4) disposed within half 80b.

As mentioned above, end effector assembly 100 is attached to the distal end 14 of shaft 12 and includes a pair of opposing jaw members 110 and 120. Movable handle 40 of handle assembly 30 is ultimately connected to a drive rod 32 (FIG. 4) that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. As best seen in FIG. 3, movable handle 40 is selectively moveable about a pivot 69 from a first position relative to fixed handle 50 to a second position in closer proximity to the fixed handle 50 that imparts movement of the jaw members 110 and 120 relative to one another.

As shown best in FIG. 3, housing 20 encloses a drive assembly 21 that cooperates with the movable handle 40 to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. The handle assembly 30 can generally be characterized as a four-bar mechanical linkage composed of the following elements: movable handle 40, a link 65, a cam-like link 36 and a base link embodied by fixed handle 50 and a pair of pivot points 37 and 67b. Movement of the handle 40 activates the four-bar linkage that, in turn, actuates the drive assembly 21 for imparting movement of the opposing jaw members 110 and 120 relative to one another to grasp tissue therebetween.

Fixed handle 50 includes a channel 54 defined therein that is dimensioned to receive a flange 92 that extends proximally from movable handle 40. Flange 92 includes a fixed end 90 that is affixed to movable handle 40 and a t-shaped free end 93 that is dimensioned for facile reception within channel 54 of handle 50 to lock and thereafter release the moveable handle 40 from handle 50 for tissue manipulation and treatment.

Housing half 20a includes proximal and distal ends 301a and 303a, respectively. Proximal end 301a is dimensioned to receive the electrical sleeve 99 that secures the electrosurgical cable 310 (FIG. 1) within the housing 20. As best shown in FIG. 3, paired cable 310 splits into two electrosurgical cable leads 310a and 310b that are subsequently fed through the housing 20 to ultimately transmit different electrical potentials to the opposing jaw members 110 and 120.

The distal end 303a is generally arcuate in shape such that, when assembled, distal ends 303a and 303b form a collar 303 (FIG. 4) that extends distally from the housing 20 to mechanically engage the rotating assembly 80.

The handle assembly 30, that includes the above-mentioned fixed handle 50 and movable handle 40, also includes the cam link 36 that is generally triangular in shape. The cam link 36 includes an upper piston 38, a fixed pivot 37 and a handle pivot 69. More particularly, fixed pivot 37 is rotatingly mounted within fixed mounts 329a and 329b between opposing housing halves 20a and 20b and the handle pivot 69 is rotatingly mounted within the bifurcated end of handle 40 through apertures 68a and 68b. Cam piston 38 is poised within a longitudinal channel 25c defined through the drive assembly 21 (explained in further detail below with respect to the discussion of the drive assembly 21) in abutting relationship with a compression tab 25 such that movement of the handle 40 rotates piston 38 proximally against a coil spring 22.

Link 65 is also associated with the handle assembly 30 and forms an integral part of the four-bar mechanical linkage. Link 65 includes a distal end 63 and two pivot pins 67a and 67b. Pivot pin 67a engages apertures 68a and 68b disposed within the movable handle 40 and pivot 67b engages fixed mounts 331a and 331b between housing halves 20a and 20b such that movement of the handle 40 towards fixed handle 50 pivots link 65 about pivots 67a and 67b.

A drive assembly 21 is positioned within the housing 20 between housing halves 20a and 20b. As discussed above, the drive assembly 21 includes the previously described drive rod 32 and the compression mechanism 24. Compression mechanism 24 includes a compression sleeve 27 that is telescopically and/or slidingly disposed within a spring mount 26. The distal end 28 of the compression sleeve 27 may be C-shaped and dimensioned to engage the tab 33 disposed at the proximal end of drive rod 32 such that longitudinal movement of the compression sleeve 27 actuates the drive rod 32. The proximal end of the compression sleeve 27 is dimensioned to engage a barbell-shaped compression tab 25 that is disposed within a longitudinal slot 25s of the spring mount 26. The compression sleeve 27 also includes a longitudinal slot or channel 25c that is longitudinally aligned with slot 25s and is dimensioned to receive the cam piston 38 of the cam link 36 described above.

The proximal end of spring mount 26 includes a circular flange (e.g., nut 23) that is dimensioned to bias the compression spring 22 once the compression mechanism 24 is assembled and seated within housing 20 (FIG. 3). The distal end of spring mount 26 includes a flange 25f that restricts distal movement of the tab 25 to within the slot 25s of the spring mount 26 and biases the opposite end the spring 22. The nut 23 includes an internal thread and can be rotated around the spring mount 26 to adjust the compression of the spring 22. Compression of the spring 22 may be viewed through one or more windows 340 disposed within the housing halves, e.g., 20b.

FIG. 4 also shows the trigger assembly 70 that is dimensioned to reciprocate the knife tube 34. A torsion spring 75 may also be incorporated within the trigger assembly 70 to facilitate progressive and consistent longitudinal reciprocation of the trigger assembly 70 and knife tube 34 to assure reliable separation along the tissue seal.

As mentioned above, manufacturing an instrument that provides appropriate closure force between opposing electrode within a pressure range of about 3 kg/cm$^2$ to about 16 kg/cm$^2$ is often difficult especially due to the inherent difficulties of accurately determining the closure force between the jaw members 110 and 120 after assembly. Relying on a surgeon to manually provide the appropriate closure force within the appropriate range on a consistent basis would be difficult and the resultant effectiveness and quality of each seal would vary. As a result, it is important to lock moveable handle 40 relative to handle 50 to produce the appropriate closure force to seal tissue. For example, one of the inherent difficulties of accurately measuring the closure force includes measuring the closure force in a non-destructive fashion (e.g., placing a measuring device, such as a strain gauge or pressure sensitive film, between the jaw members 110 and 120 interferes with the final angle of the jaw members, thereby interfering with the measurement).

FIGS. 5 and 6 illustrate a system 700 for calibration of the compression mechanism 24. Prior to assembly of the drive assembly 21 into the housing 20, the drive assembly 21 is coupled to the shaft 12, which in turn is coupled to the opposing jaw members 110 and 120. Thereafter, the drive assembly 21 is loaded into the system 700, which includes a base 701 having a distal support member 702 and a proximal support member 703. The distal and proximal support members 702 and 703 each have a groove 704 and 705 defined therein, respectively, configured to accommodate and frictionally engage the shaft 12. As the drive assembly 21 is placed into the grooves 704 and 705 of the distal and proximal support members 702 and 703, the shaft 12 is held in place due to frictional engagement with the walls of the distal and proximal support members 702 and 703. To further secure the shaft 12 and the drive assembly 21 to the system 700, a locking member 706 may be utilized to secure the shaft 12 in place. Specifically, the locking member 706 is rotatably attached to the upper surface of the proximal support member 703 and configured to rotate thereabout. The locking member 706 may be rotated about the proximal support member 703 into a locking position to cover the groove 705 having the shaft 12 accommodated therein. When the locking member 706 is rotated into the locking position to cover the shaft 12 in the groove 705, the shaft 12 is prevented from releasing and/or "popping out" of the proximal support member 703.

As discussed above, the drive assembly 21 includes the compression mechanism 24 having the compression spring 22. The compression mechanism 24 rests proximally of the support member 703 such that the compression mechanism 24 is secured between a compression holder 707 and a bracket 709, which prevents rotation of the drive assembly 21 and the shaft 12 about the longitudinal axis thereof. Thus, the support members 702 and 703 along with the compression holder 707 secure the drive assembly 21 to the base 701 preventing any movement thereof.

Once the drive assembly 21 is secured to the base 701, the proximal end of the drive assembly 21, namely, the nut 23, mechanically interfaces with a compression adjustment mechanism 712 having a rotating assembly 714 with a socket 710 coupled thereto. More specifically, the nut 23 interfaces with the socket 710, which has an inner-surface having the same number of planar surfaces as the nut 23 (e.g., six). In embodiments, the nut 23 and the socket 710 may include any number of corresponding surfaces.

The rotating assembly 714 is slidably coupled to a support member 715, allowing the rotating assembly 714 to slide along the longitudinal axis thereof in either a proximal or a distal direction. This allows the rotating assembly 714 to be moved in a proximal direction while the drive assembly 21 is loaded into the base 701 and then to be brought into mechanical contact therewith once the drive assembly 21 is secured. Further, the rotating assembly 714 includes a gear 716 that interfaces with a drive motor 718 through a reducer gear 720. During operation, the drive motor 718 is activated and rotates the reducer gear 720 in a counter-clockwise direction thereby rotating the gear 716 of the rotating assembly 714 in the correspondingly opposite direction (i.e., clockwise). Rotation of the gear 716 thereafter is translated to the nut 23 through the socket 710, thereby moving the nut 23 in either the distal or the proximal direction. As the longitudinal position of the nut 23 is adjusted by the drive motor 718, the compression of the spring 22 is adjusted accordingly.

The compression holder 707 is characterized by a bracket-like structure with a portion thereof being coupled to a load cell 722 and the other portion being in mechanical contact with the compression spring 22, such that the compression force of the compression spring 22 is translated to the compression holder 707. The load cell 722 is configured to measure the compression force of the compression spring 22. Thus, as the nut 23 is rotated about the spring mount 26, the load cell 722 continually measures the changes in the compression force due to the changes in the deflection of the compression spring 22.

During manufacture of the forceps 10, the compression of the compression spring 22 may be within a predetermined range such that a predetermined amount of closure force is maintained by the jaw members 110 and 120. Because of part tolerances, the amount of deflection of the compression spring 22 that is required to provide the requisite compression force is unknown. The system 700 provides for automatically adjusting the deflection of the compression spring 22 to arrive at a desirable compression force produced by the compression spring 22.

The system 700 includes a controller 724 having a programmable logic controller (not explicitly shown) or any suitable other type of logic circuit (e.g., microprocessor). The controller 724 also includes an output display 726 and an input 728 (e.g., a keypad, etc.). During operation, the drive assembly 21 is loaded into the base 701 and the socket 710 of the rotating assembly 714 is fitted around the nut 23. The load cell 722 then measures the initial compression force provided by the compression spring 22.

The load cell 722 is operatively coupled (e.g., via electrical connection) to the controller 724. The load cell 722 transmits the measured compression force to the controller 724, which then determines whether the measured compression force is within a predetermined range (e.g., from about 7 kg/cm² to about 13 kg/cm²). If the compression force is outside the predetermined range, the controller 724 commences a compression adjustment. Specifically, the controller 724 signals the drive motor 718 to rotate in a predetermined direction to rotate the gear 716 via rotation of the reducer gear 720 to rotate the nut 23 in the desired direction. In the illustrated embodiment, the drive motor 718 and, thus, the gear 716 via the reducer gear 720, are rotated in a clockwise direction to move the nut 23 in a proximal direction and compress the compression spring 22 to increase the deflection and the compression force of the compression spring 22. The drive motor 718 and, thus, the gear 716 via the reducer gear 720, are rotated in a counter-clockwise direction to move the nut 23 in a distal direction to stretch the compression spring 22 to decrease the deflection and the compression force thereof.

The controller 724 signals the drive motor 718 to adjust the nut 23 in predetermined increments. After each adjustment, the load cell 722 again measures the compression force to determine if the measured compression force is within the predetermined range. The controller 724 iteratively deflects the compression spring 22 by turning the nut 23 in the desired direction, thereby moving the compression spring 22 in the desired direction, e.g., proximal if the compression force needs to be increased, distal if the compression force needs to be decreased, until the measured compression force is within the predetermine range. Once the compression force is within the predetermined range, the controller 724 makes no further adjustments and signals the user, via the output display 726, that the adjustment is complete. The rotating assembly 714 is thereafter moved in the proximal direction along the longitudinal axis of the support member 715 to disengage from the drive assembly 21 and release the nut 23. Thereafter, the locking member 706 is opened allowing the drive assembly 21 along with the shaft 12 to be removed for further assembly into the forceps 10.

Figure 7:
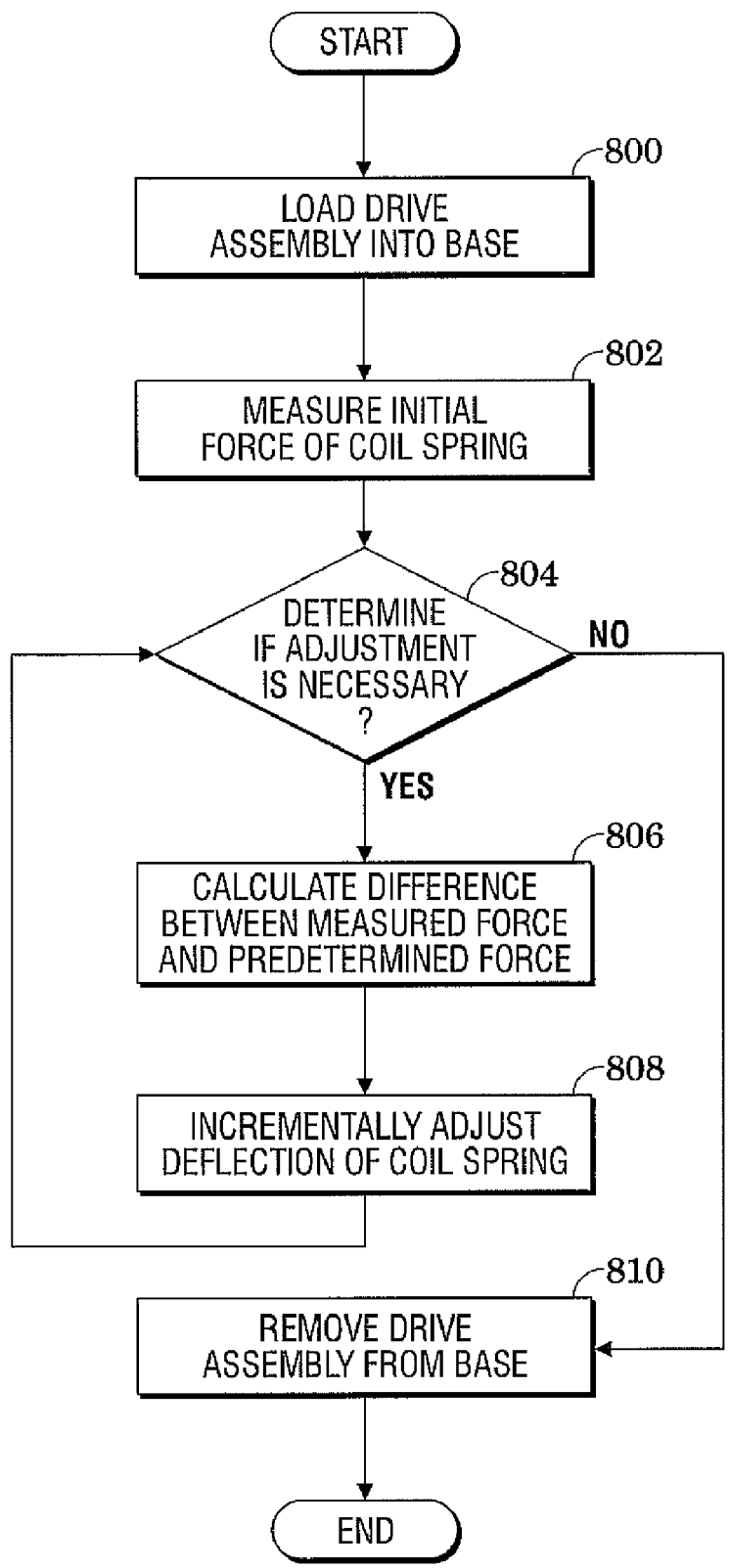
FIG. 7 is a flow chart diagram of a method for setting a force of a compression mechanism according to an embodiment of the present disclosure.

FIG. 7 illustrates a method for adjusting the compression force of the compression spring 22. In step 800, after the jaw members 110 and 120, the shaft 120, and the drive assembly 21 are manufactured and assembled, these components are loaded and secured to the base 701. In step 802, the load cell 722 is coupled to the compression holder 707 which is in turn coupled to the compression mechanism 24. The load cell 722 measures the initial compression force as a function of the deflection of the compression spring 22. The load cell 722 then transmits the measured compression force as a voltage signal to the controller 724 which then determines whether the measured compression force is within the predetermined range. In one embodiment, the user may program the controller 724 to select the desired compression force range for the compression spring 22 based on the type of forceps 10 being assembled.

In step 804, the controller 724 determines whether the deflection of the compression spring 22 needs to be adjusted in order to bring the compression force produced by the compression spring 22 into the predetermined range. If the measured compression force is outside the predetermined range, in step 806, the controller 724 determines the difference between the initial measured compression force and the predetermined range to determine the amount of adjustment to the deflection of the compression spring 22 that needs to be made in order to bring the spring 22 to the proper deflection to produce the desired compression force. This determination gives an estimate to the controller 724 on which the controller 724 bases the amount of rotation that needs to be imparted on the nut 23 in order to deflect the compression spring 22 by the desired amount.

In step 808, the controller 724 signals the drive motor 718 to incrementally adjust the nut 23 and thereby adjust the deflection of the compression spring 22. After each incremental adjustment, the controller 724 temporarily terminates the rotation of the motor 718 to measure the compression force of the compression spring 22 via the load cell 722. If the measured compression force is outside the predetermined range, the adjustments continue in steps 806 and 808. If the measured compression force is within the predetermined range and no further adjustments are necessary, the method proceeds to step 810, during which the drive assembly 21 is removed from the base 701 and thereafter assembled into the forceps 10.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A system for manufacturing forceps comprising:
   a forceps having first and second opposing jaw members;
   a compression mechanism coupled to the pair of opposing jaw members, the compression mechanism including a spring configured to provide and maintain a compression force between the opposing jaw members;
   a load cell configured to measure an initial compression force between the opposing jaw members as a function of a deflection of the spring; and
   a controller coupled to the load cell and configured to deflect the spring based on a comparison between the initial compression force and a predetermined range to adjust the compression force between the opposing jaw members.

2. A system according to claim 1, wherein the compression mechanism includes:
   a coil spring having a predetermined deflection and biased against a nut, wherein the compression force is provided as a function of the predetermined deflection.

3. A system according to claim 2, further comprising:
   a motor electrically coupled to the controller and mechanically coupled to the nut, the motor configured to rotate the nut in a first direction to increase the compression force and in a second direction to decrease the compression force in response to a signal from the controller.

4. A system according to claim 2, wherein the nut is rotated iteratively in predetermined increments until the compression force is within the predetermined range.

5. A method for manufacturing forceps comprising the steps of:
   providing a forceps having first and second opposing jaw members;
   providing a compression mechanism including a spring coupled to the pair of opposing jaw members, the spring configured to provide and maintain a compression force between the opposing jaw members;
   measuring an initial compression force between the opposing jaw members as a function of a deflection of the spring; and
   adjusting the compression force based on a comparison between the initial compression force and a predetermined range.

6. A method according to claim 5, wherein the compression mechanism of the providing step includes:
   providing a coil spring biased against a selectively adjustable nut.

7. A method according to claim 6, wherein the adjustment step further includes the steps of
   rotating the nut in a first direction to increase the compression force; and
   rotating the nut in a second direction to decrease the compression force.

8. A method according to claim 6, wherein the adjustment step further includes the step of:
   rotating the nut iteratively in predetermined increments until the compression force is within a predetermined range.

9. A method according to claim 6, further comprising the step of manufacturing each jaw member such that specifications of each jaw member fall within an acceptable manufacturing range, the specifications being selected from the group consisting of: surface area of each jaw member, distance from a pivot of each jaw member to a centroid of a sealing surface of each jaw member; angle between a cam slot of each jaw member and a line perpendicular to the sealing surface of each jaw member; distance from the cam slot to the pivot of each jaw member; and a width of the cam slot of each jaw member.

10. A method according to claim 6, wherein the compression mechanism of the providing step further includes:
   a coil spring having a predetermined deflection and biased against the selectively adjustable nut, wherein the compression force is provided as a function of the predetermined deflection.

11. A method according to claim 10, wherein the providing step further includes the step of:
   providing a controller electrically coupled to a motor that is mechanically coupled to the selectively adjustable nut.

12. A method according to claim 10, wherein the adjustment step further includes the steps of
   rotating the selectively adjustable nut in a first direction to increase the compression force; and
   rotating the selectively adjustable nut in a second direction to decrease the compression force.

13. A method according to claim 10, wherein the adjustment step further includes the step of:
   rotating the selectively adjustable nut iteratively in predetermined increments until the compression force is within the predetermined range.

* * * * *